Figure 1:
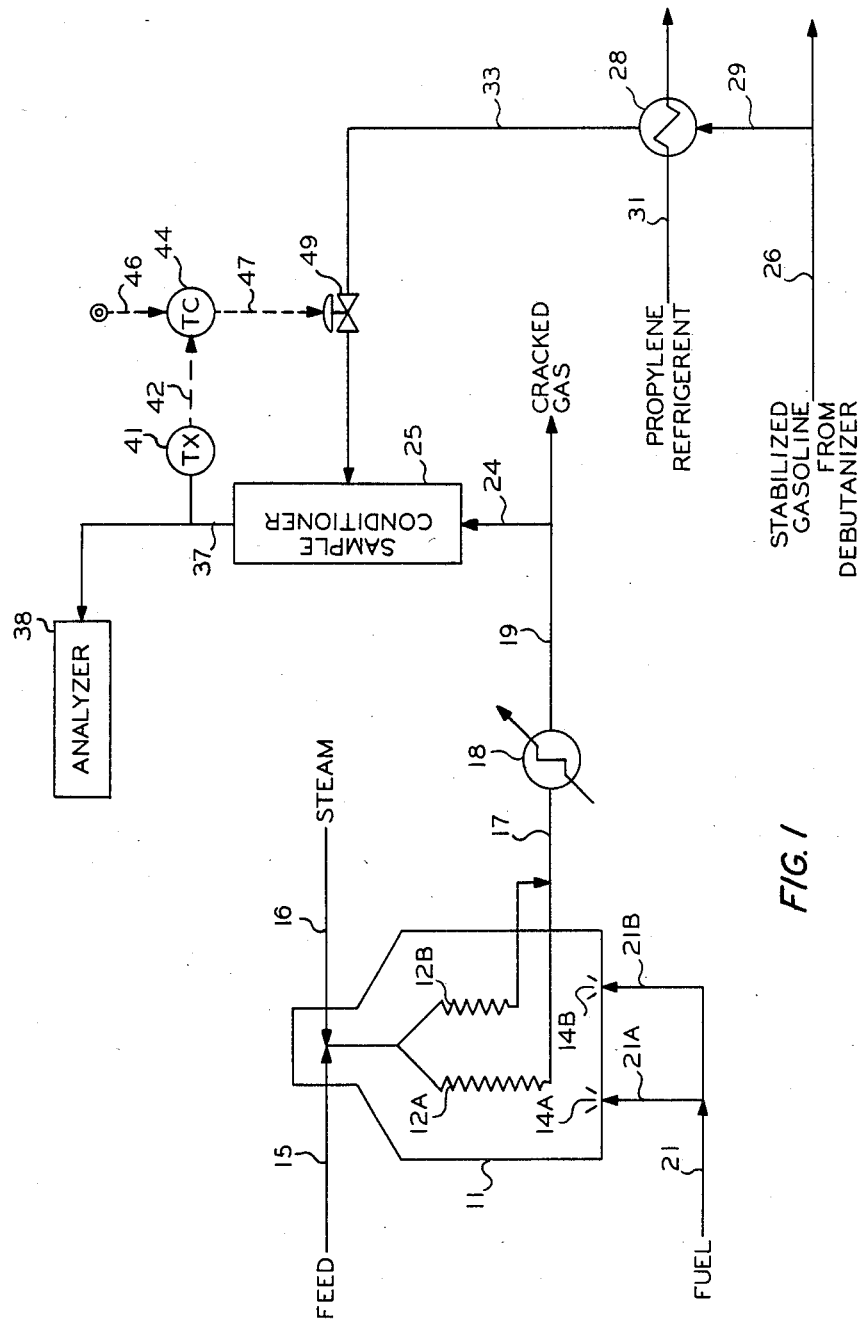

United States Patent [19]

Steed

[11] Patent Number: 4,595,397
[45] Date of Patent: Jun. 17, 1986

[54] SAMPLE CONDITIONING

[75] Inventor: Philip V. Steed, Bartlesville, Okla.

[73] Assignee: Phillips Petroleum Company, Bartlesville, Okla.

[21] Appl. No.: 421,225

[22] Filed: Sep. 22, 1982

[51] Int. Cl.$^4$ .......................................... B01D 47/00
[52] U.S. Cl. .................................. 55/37; 55/48; 55/67; 55/227; 55/233
[58] Field of Search .............. 55/20, 37, 48, 67, 68, 55/233, 226, 227

[56] References Cited

U.S. PATENT DOCUMENTS

| | | | |
|---|---|---|---|
| 2,661,812 | 12/1953 | Gilmore | 55/20 |
| 3,076,301 | 2/1963 | Roof | 55/18 |
| 3,391,577 | 7/1968 | Friauf et al. | |
| 3,438,261 | 4/1969 | Collins, Jr. | |
| 3,446,077 | 5/1969 | Sanford et al. | 55/210 |
| 3,470,069 | 9/1969 | Bracken et al. | 55/20 |
| 3,581,473 | 6/1971 | Ririe, Jr. et al. | 55/219 |
| 3,675,489 | 7/1972 | Garilli et al. | |
| 3,719,029 | 3/1973 | Suzukawa et al. | 55/91 |
| 3,988,919 | 11/1976 | Talmi et al. | 55/67 |
| 4,235,613 | 11/1980 | Castoe et al. | 55/68 |

FOREIGN PATENT DOCUMENTS 1556933 12/1979 United Kingdom .

Primary Examiner—John Adee
Attorney, Agent, or Firm—French and Doescher

[57] ABSTRACT

Conditioning of a sample of the cracked-gas effluent from a cracking furnace is accomplished by contacting the sample under suitable conditions with a suitable hydrocarbon absorbent in such a manner that the heavier components in the cracked-gas sample are absorbed. The rate at which the sample is contacted with the suitable hydrocarbon absorbent is controlled so as to maintain a desired composition of the conditioned sample.

14 Claims, 2 Drawing Figures

SAMPLE CONDITIONING

This invention relates to sample conditioning. In one aspect, this invention relates to method and apparatus for obtaining a desired sample for analysis from the cracked-gas effluent flowing from a cracking furnace.

The cracking furnace forms the heart of many chemical manufacturing processes. Often, the performance of the cracking furnace will carry the burden of the major profit potential for the entire manufacturing process. Close control of the cracking furnace is required to maximize the performance of the cracking furnace.

In a manufacturing process such as the manufacture of ethylene, a feedstock such as ethane and/or propane and/or naphtha is fed together with a diluent fluid such as steam into the cracking furnace. Within the furnace the feed gas is converted to a gaseous mixture which primarily contains hydrogen, methane, ethylene, propylene, butadiene and small amounts of heavier gases. At the furnace exit, this mixture is generally cooled in a transfer line heat exchanger.

An analysis of the effluent flowing from the cracking furnace can be utilized to provide an indication of the manner in which the cracking furnace is performing. Often, such an analysis provides an indication of a change in some operating condition which will improve the performance of the cracking furnace.

If it is desired to analyze only the lighter components in the effluent flowing from the cracking furnace, it is necessary to provide a sample conditioning system which removes heavier components from the effluent. In the past, fractionation schemes or water separation schemes have been utilized. However, these schemes have disadvantages such as requiring extra energy in the case of fractionation or requiring a procedure for removing water in the case of a water separation.

It is thus an object of this invention to provide method and apparatus for obtaining a desired sample of the lighter components in the cracked gas effluent from a cracking furnace for chromatographic analysis.

In accordance with the present invention, method and apparatus is provided whereby a sample of the cracked gas effluent from a cracking furnace is contacted under suitable conditions with a suitable hydrocarbon adsorbent in such a manner that the heavier components in the cracked gas sample are absorbed. The lighter components are removed from the sample conditioning system and may be provided to an analyzer. The flow rate of the absorbent hydrocarbon to the sample conditioning system is manipulated so as to maintain a desired composition of the sample stream provided to the analyzer. In this manner, a desired sample of the cracked gas effluent from a cracking furnace is provided for analysis.

Figure 2:
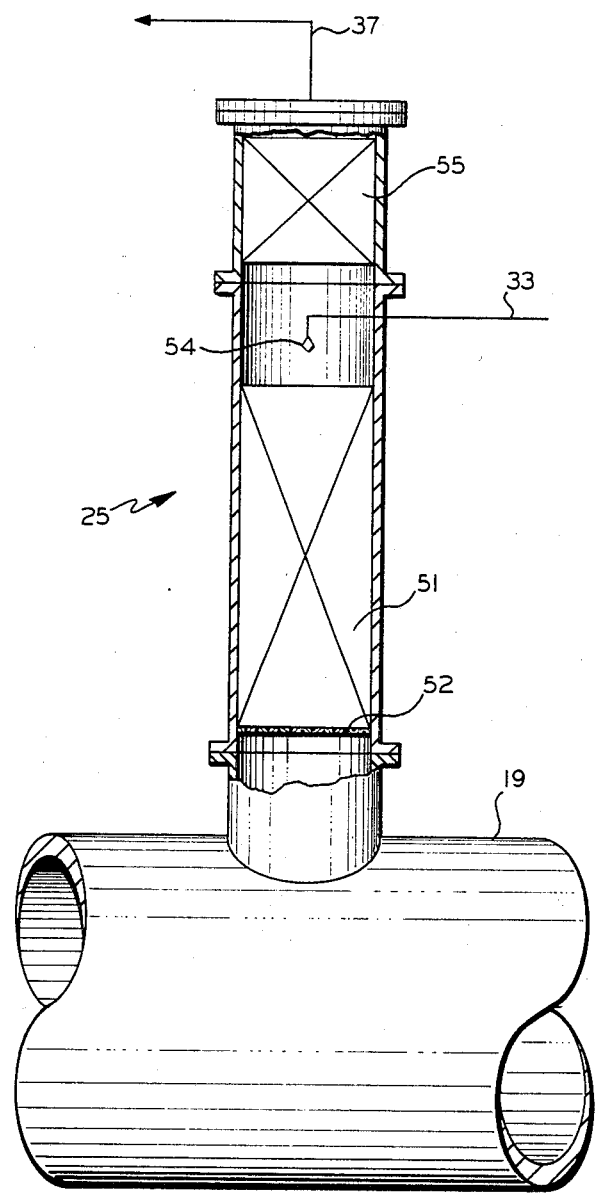

Other objects and advantages of the invention will be apparent from the foregoing brief description of the invention and the claims as well as the detailed description of the drawings in which:

FIG. 1 is a diagrammatic illustration of a cracking process and the sample conditioning system of the present invention; and FIG. 2 is a detailed illustration of the sample conditioning system of the present invention.

The invention is illustrated and described in terms of a process for the manufacture of ethylene. However, the applicability of the invention described herein extends to other processes wherein a cracking furnace is utilized to crack a feed into some desired components.

Referring now to FIG. 1, a conventional cracking furnace 11 is illustrated having two cracking tubes 12a and 12b. Heat is supplied to the two cracking tubes 12a and 12b by means of burners 14a and 14b, respectively.

A feedstock such as ethane and/or propane and/or naphtha is provided as a feed to the cracking furnace 11 through conduit means 15. Steam is provided to the cracking furnace 11 through conduit means 16. The feed gas flowing through conduit means 15 and the steam flowing through conduit means 16 are combined within the cracking furnace 11 and flow through the cracking tubes 12a and 12b. After passing through the cracking tubes 12a and 12b, in which the feed is converted to ethylene, propylene and other gases, the gaseous mixture is combined and flows through conduit means 17 to the transer line heat exchanger 18 in which the effluent from the cracking furnace 11 is cooled. From the transfer line heat exchanger 18, the gaseous mixture flows to various distillation columns through conduit means 19.

Fuel is supplied to the cracking furnace 11 through conduit means 21. Specifically, fuel is supplied to burner 14a through conduit means 21a which is operatively connected to conduit means 21. Fuel is supplied to burner 14b through conduit means 21b which is also operatively connected to conduit means 21.

The cracking furnace described to this point is a conventional cracking furnace. It is the manner in which a sample of the cracked gas effluent flowing through conduit means 19 is conditioned which provides the novel features of the present invention.

A sample of the effluent flowing through conduit means 19 is provided through conduit means 24 to the sample conditioner 25 and passes upflow through the sample conditioner 25. The sample conditioner 25 will be described more fully with reference to FIG. 2.

Stabilized gasoline, which is removed as a bottoms product from the debutanizer associated with the ethylene manufacturing process, flows through conduit means 26. A portion of the stabilized gasoline flowing through conduit means 26 is provided to the heat exchanger 28 through conduit means 29. Propylene refrigerant, which is also available in the ethylene manufacturing process, is provided as a cooling medium to the heat exchanger 28 through conduit means 31. Cooling of the stabilized gasoline increases its capacity to absorb gases. The thus cooled, stabilized gasoline is removed from the heat exchanger 29 and provided through conduit means 33 to the sample conditioner 25. The cold, stabilized gasoling passes downflow through the sample conditioner 25.

In the sample conditioner 25, the cold, stabilized gasoline is contacted with the gas flowing through conduit means 24. Heavier components in the gas flowing through conduit means 24 are absorbed by the stabilized gasoline. Lighter components is the gas flowing through conduit means 24 are removed from the sample conditioner 25 through conduit means 37 and are provided to the analyzer 38, which is a chromatographic analyzer such as the Model 102 process analyzer manufactured by Applied Automation, Inc. Bartlesville, Okla. p Temperature transducer 41 in combination with a temperature-sensing device such a thermocouple, which is operably located in conduit means 37, provides an output signal 42 which is representative of the actual temperature of the gas flowing through conduit means 37. There is a direct correlation between the temperature of the gas flowing through conduit means 37 and the composition of the gas since higher temperatures are required to maintain the heavier components in a gaseous form. Signal 42 is provided from the temperature transducer 41 as the process variable input to the temperature controller 44.

The temperature controller 44 is also provided with a set point signal 46 which is representative of the desired temperature of the gas flowing through conduit means 37. The temperature represented by signal 47 is selected based on the desired composition of the gas flowing through conduit means 37. Thus, a change in the temperature represented by signal 46 can result in more or less of the heavier components being removed from the effluent sample flowing through conduit means 24.

In response to signals 42 and 46, the temperature controller 44 provides an output signal 47 which is responsive to the difference between signals 42 and 46. Signal 47 is scaled so as to be representative of the position of the control valve 49, which is operably located in conduit means 33, required to maintain the actual temperature of the gas flowing through conduit means 37 substantially equal to the desired temperature represented by signal 46. Signal 47 is provided from the temperature controller 44 as a control signal to the control valve 49 and the control valve 49 is manipulated in response thereto.

Referring now to FIG. 2, in the lower portion of the sample conditioner 25 is filled with a packing material 51 which is suitable for good vapor-liquid contacting. Any suitable material may be used. Ceramic berl saddles are presently preferred. The column packing is supported on the screen 52.

Stabilized gasoline is sprayed onto the column packing through the spray nozzle 54. The spray nozzle 54 is utilized to ensure a uniform distribution of the stabilized gasoline on the column packing 51.

The affluent flowing from conduit means 19 is contacted with the stabilized gasoline in the column packing 51 and the heavier components of the effluent flowing through conduit means 19 are absorbed. The lighter components flow through the packing 55, which is utilized to ensure adequate vapor-liquid separation, and then through conduit means 37 to the chromatographic analyzer 38 illustrated in FIG. 1. The heavy components, together with the stabilized gasoline, are returned to conduit means 19.

Any suitable material can be utilized for the packing 55. Stainless steel wool is presently preferred.

The use of a stabilized gasoline as an absorbent is presently preferred because the stabilized gasoline is a good absorbent and is readily available in an ethylene plant. Any suitable hydrocarbon containing absorbing agent could be utilized. Generally, such suitable hydrocarbon containing absorbing agents are characterized by having a boiling range above about 100° F.

The invention has been described in terms of a preferred embodiment as illustrated in FIGS. 1 and 2. Specific components which can be used in the practice of the invention have been described. The temperature transducer 41, temperature controller 44, and control valve 49 are each well known, commercially available control components such as are illustrated and described at length in Perry's Chemical Engineers Handbook, Fourth Edition, Chapter 22, McGraw-Hill.

While the invention has been described in terms of the presently preferred embodiment, reasonable variations and modifications are possible by those skilled in the art and such variations and modifications are within the scope of the described invention and the appended claims.

That which is claimed is:

1. Apparatus comprising:
   a cracking furnace means;
   means for supplying a hydrocarbon-containing feed stream to said cracking furnace means;
   means for removing a gaseous mixture, containing the products being produced from the cracked components of said feed stream, from said cracking furnace means;
   means for contacting a portion of said gaseous mixture with a suitable hydrocarbon-containing absorbent stream, wherein some of the heavy components in said gaseous mixture are absorbed by said absorbent stream;
   means for removing a conditioned stream containing the lighter components in said gaseous mixture from said means for contacting said gaseous mixture and said absorbent stream;
   a debutanizer column;
   means for removing stabilized gasoline as a bottoms product from said debutanizer column;
   a heat exchange means;
   means for providing a refrigerant to said heat exchange means; and
   means for passing a portion of said stabilized gasoline through said heat exchange means to thereby produce said absorbent stream.

2. Apparatus in accordance with claim 1 wherein said means for contacting a portion of said gaseous mixture and said absorbent stream comprises:
   a column containing a first packing material suitable for vapor-liquid contacting;
   means for passing said portion of said gaseous mixture upflow through said first packing material; and
   means for spraying said absorbent stream on the top of said first packing material, wherein said absorbent stream passes downflow through said first packing material and wherein said portion of said gaseous mixture passes in contact with said absorbent stream in said first packing material.

3. Apparatus in accordance with claim 2 wherein said column additionally contains a second packing material suitable for vapor-liquid separation located at a position such that the lighter components of the portion of said gaseous mixture which is contacted with said absorbent stream flow through said second packing material after being contacted with said absorbent stream.

4. Apparatus in accordance with claim 3 wherein said first packing material is ceramic berl saddles and said second packing material is stainless steel wool.

5. Apparatus in accordance with claim 1 additionally comprising:
   a chromatographic analyzer; and
   means for providing said conditioned stream to said chromatographic analyzer.

6. Apparatus in accordance with claim 1 additionally comprising:
   means for establishing a first signal representative of the actual temperature of said conditioned stream;
   means for establishing a second signal representative of the temperature of said conditioned stream required to maintain a desired composition for said conditioned stream;

means for comparing said first signal and said second signal and for establishing a third signal which is responsive to the difference between said first signal and said second signal; and means for manipulating the rate at which said absorbent stream is contacted with said portion of said gaseous mixture in response to said third signal so as to maintain the actual temperature of said conditioned stream substantially equal to the desired temperature represented by said second signal.

7. Apparatus in accordance with claim 7 wherein said refrigerant is propylene.

8. A method for conditioning a sample of the gaseous mixture from a cracking furnace, wherein said gaseous mixture contains the products produced by the cracking of a hydrocarbon-containing feed stream supplied to said cracking furnace, said method comprising the steps of:

contacting a portion of said gaseous mixture with a suitable hydrocarbon containing absorbent stream, wherein some of the heavy components in said gaseous mixture are absorbed by said absorbent stream;

removing a conditioned stream containing the lighter components in said gaseous mixture as a conditioned sample;

removing stabilized gasoline as a bottoms product from a debutanizer column; and passing said stabilized gasoline in contact with a refrigerant to produce said absorbent stream.

9. A method in accordance with claim 8 wherein step of contacting said portion of said gaseous mixture with said absorbent stream comprises:

passing said portion of said gaseous mixture upflow through a first packing material suitable for vapor-liquid contacting; and spraying said absorbent stream on the top of said first packing material, wherein said absorbent stream passes downflow through said first packing material and wherein said portion of said gaseous mixture passes in contact with said absorbent stream in said first packing material.

10. A method in accordance with claim 9 additionally comprising the step of passing said gaseous mixture through a second packing material suitable for vapor-liquid separation after said portion of said gaseous mixture has been contacted with said absorbent stream in said first packing material.

11. A method in accordance with claim 10 wherein said first packing material is ceramic berl saddles and said second packing material is stainless steel wool.

12. A method in accordance with claim 9 additionally comprising the step of providing said conditioned stream to a chromatographic analyzer.

13. A method in accordance with claim 8 additionally comprising the steps of:

establishing a first signal representative of the actual temperature of said conditioned steam;

establishing a second signal representative of the temperature of said conditioned stream required to maintain a desired composition for said conditioned stream;

comparing said first signal and said second signal and establishing a third signal which is responsive to the difference between said first signal and said second signal; and manipulating the rate at which said absorbent stream is contacted with said portion of said gaseous mixture in response to said third signal so as to maintain the actual temperature of said conditioned stream substantially equal to the desired temperature represented by said second signal.

14. A method in accordance with claim 13 wherein said refrigerant is propylene.

* * * * *

UNITED STATES PATENT AND TRADEMARK OFFICE
CERTIFICATE OF CORRECTION

PATENT NO. : 4,595,397

DATED : June 17, 1986

INVENTOR(S) : Philip V. Steed

It is certified that error appears in the above-identified patent and that said Letters Patent is hereby corrected as shown below:

In column 5, line 11, delete "7" and insert --- 6 ---.

In column 5, line 14, after "mixture" and before "from" insert --- removed ---.

Signed and Sealed this

Twenty-third Day of December, 1986

Attest:

DONALD J. QUIGG

Attesting Officer

Commissioner of Patents and Trademarks